United States Patent [19]

Itil et al.

[11] 4,330,538

[45] May 18, 1982

[54] USE OF ESTRADIOL VALERATE AS AN ANTI-DEPRESSANT

[75] Inventors: Turan M. Itil, Nyack, N.Y.; Gerhard Laudahn; Werner M. Herrmann, both of Berlin, Fed. Rep. of Germany

[73] Assignee: Schering Aktiengesellschaft, Berlin and Bergkamen, Fed. Rep. of Germany

[21] Appl. No.: 972,626

[22] Filed: Dec. 22, 1978

[30] Foreign Application Priority Data

Dec. 23, 1977 [DE] Fed. Rep. of Germany ....... 2758549

[51] Int. Cl.$^3$ ...................... A01N 45/00; A61K 31/56

[52] U.S. Cl. .................................................... 424/238
[58] Field of Search ........................................ 424/238

[56] References Cited

U.S. PATENT DOCUMENTS 4,145,416  3/1979  Lachnit-Fixson et al. ......... 424/238

Primary Examiner—Elbert L. Roberts
Attorney, Agent, or Firm—Millen & White

[57] ABSTRACT

Estradiol valerate has been discovered to possess neuropsychotropic activity, e.g., it is an effective anti-depressant having advantageous properties.

9 Claims, No Drawings

USE OF ESTRADIOL VALERATE AS AN ANTI-DEPRESSANT

BACKGROUND OF THE INVENTION

This invention relates to a new use of estradiol valerate as a medicinal agent, i.e., having neuropsychotropic activity, particularly anti-depressant properties.

Estradiol 17-n-valerate (estra-1,3,5(10)-triene-3-ol-17β-valerate) has been known as an estrogen for a long time in medical practice.

It is furthermore known that several steroids exert an attenuating effect on the central nervous system and possess hypnotic and/or anesthetic effects. However, these steroids have no significance as medicinal agents in the indications of the present invention, since they lead, for example, to a strong depression of the central nervous system.

It is also known that, when the amount of sexual hormones which are natural to the body and have a steroid structure, is reduced, for example, during the climacterium, the psychic disturbances associated with such a deficit can be overcome by administration of endocrinically active steroids.

However, this effect is of no significance with respect to the pharmacological use of this invention, i.e., in relation to general anti-depressant activity, since this prior art use involves substitution therapy limited to steriod deficiency. According to this invention, estradiol valerate is effective for all types of depressions in women such as, for example, psychotic depressions (manic-depressive psychosis, endogenic depression), neurotic depressions, and reactive depressions not connected with endocrinological disturbances. In these indications, a substantially higher dosage is required in this invention than in the case of substitution therapy.

It is further known that conjugated estrogens may exert an anti-depressive effect upon oral administration to depressed female patients, (E. L. Itil et al., Spectrum Publications, 1977, pp. 135). However, this disclosure also has no significant relevance to this invention, since estradiol 17-n-valerate is not a member of the class of conjugated estrogens, which are metabolites and excretion products of estrogen metabolism.

Also known as active psychopharmaceuticals having anti-depressant effects are the so-called tricyclic anti-depressants, such as amitriptyline, imipramine, and desipramine; and also monoamine oxidase (MAO) inhbitors, such as nialamide and pargyline; as well as stimulants of the amphetamine type. These active agents have the property in common of possessing a high toxicity. Furthermore, they have the disadvantage that the anti-depressive effect takes weeks to develop. These disadvantages represent a high risk factor, especially for suicide-prone persons. Furthermore, these active agents have a number of side effects. Particularly undesirable side effects of the tricyclic anti-depressants are neurological and vegetative symptoms, such as, for example, visual disturbances, disturbances of cardiac rhythm, dry mouth, changes in consciousness, as well as in some cases also dangerous changes in blood components. Undesirable side effects of the MAO inhibitors are, above all, liver damage and dangerous hypertonic crises upon ingestion of tyramine-containing foods. For amphetamines, the strong CNS-stimulating and dependency-forming effect of these substances has led to the recent practical discontinuance of their use as anti-depressants.

SUMMARY OF THE INVENTION

Accordingly, it is an object of this invention to provide a new neuropsychotropic, and especially antidepressantly, active pharmaceutical composition and a method for its use which is free from the foregoing disadvantages.

Upon further study of the specification and appended claims, further objects and advantages of this invention will become apparent to those skilled in the art.

These objects have been achieved by providing a composition comprising an amount of estradiol valerate effective as a neuropsychotropic agent, especially an anti-depressant. As well, a method for treating depression in humans comprising administering an anti-depressantly effective amount of estradiol valerate is also provided.

DETAILED DISCUSSION

The pronounced anti-depressant activity of estradiol valerate was established in a placebo-controlled double-blank experiment by quantitative pharmacoelectroencephalography (CEEG) on humans. Furthermore, the effects and side effects were recorded by means of various rating scales, e.g., for neurological and psychosomatic symptomatology, by self-rating scales for sedation, anxiety, and depression, as well as by interviews conducted by psysicians.

In the practical application of estradiol valerate as an anti-depressant, the desired effect occurs only very shortly after administration, i.e., approximately after 2–3 hours. This is surprising, since, heretofore, the effects of endocrinically active steroids have been known to be felt only after a rather long period of treatment.

Another major advantage of the use of estradiol valerate as an anti-depressant resides particularly in the fact that even at individual oral doses on the order of 200 mg. there are no resultant neurological, vegetative, or other side effects. Consequently, an overdose would not, in the final analysis, lead to death.

It is also advantageous that, contrary to what is possible for known anti-depressants, no dependency is created, even during a long-term use of estradiol valerate.

The present invention, thus, relates to a method for the treatment of depressions and disturbances of mood, behavior and functional capacity by means of administering the compound of this invention. Among these disturbances are, in particular, endogenic, neurotic, and reactive depressions, depression of the aged, climacterium and involution depressions.

Moreover, the medicaments of this invention are also suitable for the treatment of weakness of ability to concentrate and memory, in persons with or without estrogen deficiency; as well as of psychophysiological diseases, such as diminishing general functional capacity, fatigue, loss of interest, and sleep disturbances, as well as insomnia at night with fatigue during the day; and also of disturbances of a sexual nature, such as loss of libido and potency in younger patients without steroid hormone deficiency.

In medical practice, the medicament compositions of this invention containing estradiol valerate can be administered intra-muscularly or orally. The daily dosage is 1–100 mg. per day, preferably 2–8 mg. per day. The dose can be administered all at once or in several increments. The foregoing dosage is that generally effective in treating all the psychic disturbances mentioned above. The usual dose is given not as a single administration, but as a continuous daily administration over prolonged period of time.

In general, the administration of estradiol valerate for purposes of this invention can be performed analogously to that for the conventional anti-depressants amitryptiline, imipramine, or desipramine unless otherwise specified herein.

The disease terminology used herein and the characterization of the various indications for the medicament of this invention are in accordance with conventional definitions as described, e.g., in "International Classification of Diseases, Manual of the International Statistical Classification of Diseases, Injuries, and Causes of Death, World Health Organization, Geneva, 1977 and 1978", which is incorporated by reference herein. Other specific types of psychic disorders and depressions which can be treated in accordance with this invention are also defined therein.

The medicament compositions of this invention containing estradiol valerate can be formulated conventionally by processing estradiol valerate together with the vehicles, diluents, flavor-ameliorating agents, etc. customary in galenic pharmacy and converting the product into the desired form of application, such as, for example, tablets, dragees, capsules, solutions, etc. Especially suitable for injections are oily solutions, e.g., solutions in sesame, castor, and cottonseed oil. If desired, diluents or solubilizers can be added to increase solubility, such as, for example, benzyl benzoate or benzyl alcohol. Especially advantageous for oral administration are tablets, capsules, dragees, pills, suspensions, and solutions. Typically, unit dosages are 0.5-50 mg., preferably 1-10 mg. Except as indicated otherwise herein, the pharmaceutical compositions of this invention containing estradiol valerate are fully conventional in composition and formulation methods.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

The formulation of several drug specialties are described in greater detail below by means of the following examples, wherein Aerosil is a submicroscopic pyrogenic silica of Degussa, Inc., and DAB represents German Pharmacopoeia:

EXAMPLE 1

2.0 mg. of estradiol valerate is mixed homogeneously with 133.5 mg. of lactose, 59.5 mg. of corn starch, 2.0 mg. of "Aerosil", 2.5 mg. of polyvinylpyrrolidone 25, and 0.5 mg. of magnesium stearate and then compressed into round, biplanar tablets without previous granulation; the tablets have a notch to break them apart and a final weight of 200 mg.

EXAMPLE 2

To produce an injection solution, 1.0 mg. of estradiol valerate is dissolved in a mixture of 3 parts by volume of benzyl benzoate (USP XVII) and 2 parts by volume of castor oil (DAB. 7, USP XVII); the solution is filtered in the sterile state and filled up under aseptic conditions to yield 1 ml., and dispensed into ampoules.

EXAMPLE 3

Respectively 1 mg. of estradiol valerate (micronized, particle size 2-8 $\mu$m) is mixed homogeneously with 150 mg. of lactose (DAB 7, USP XVII) and filled into hard gelatin mating capsules (5×15 mm.).

EXAMPLE 4

Analogously to Example 1, 1 mg. of estradiol valerate is combined with 119.5 mg. of lactose, 59.5 mg. of corn starch, 2.0 mg. of "Aerosil", 2.5 mg. of polyvinylpyrrolidone 25, and 0.5 mg. of magnesium stearate and compressed into tablets having a final weight of 185 mg.

EXAMPLE 4A

To produce an injection solution, 10.0 mg. of estradiol valerate are dissolved in a mixture of 3 parts by volume of benzyl benzoate (USP XVII) and 2 parts by volume of castor oil (DAB. 7, USP XVII); the solution is filtered in the sterile state and filled up under aseptic conditions to yield 1 ml., and dispensed into ampoules.

The following examples demonstrate the efficacy of estradiol valerate according to this invention on humans.

EXAMPLE 5

The patient is a 27-year-old woman who has suffered from depressions for two and one-half years. Her depressions began gradually with a feeling of sadness, with a frequent desire to scream, with a feeling of hopelessness, with anxiety, loss of appetite, and sleep disturbances. The degree and frequency of the attacks of depression changed with environmental factors. After six months, she often harbored strong depressions and thoughts of suicide. She received a number of antidepressant drugs by prescription from various physicians, but she cannot remember the names of the medicaments. These medicines helped her temporarily. However, she constantly felt extremely fatigued. Since the depressions have recently intensified and she was greatly fatigued by the antidepressants, she was treated with estradiol valerate.

Symptoms Prior to Treatment: The patient suffers medium to strong depressions. She speaks of a feeling of hopelessness and sadness. Her facial expression confirms these statements. She displays slight restlessness and anxiety, loss of appetite, and a disturbed sleep profile.

Onset of Treatment: On the eighth day after beginning of menstruation, the patient received twice 2 mg. tablets of estradiol valerate. On the second treatment day, the dose was increased to three times 2 mg. of estradiol valerate. The treatment was continued with this dosage for a period of one week.

After One Week of Treatment: After having been administered a total of 34 mg. of estradiol valerate, the patient states that her depressions have been ameliorated to a minor extent, but quite perceptibly so in the last week of treatment. Her appetite has improved somewhat, thoughts of suicide have not occurred as frequently as before. However, she still is subject to irritation and suffers from sleep disturbances.

The treatment was continued with the same daily dose of three times 2 mg. of estradiol valerate.

After Two Weeks of Treatment: After an administration of in total 76 mg. of estradiol valerate, the patient shows a relaxed, calm, and happy attitude. She states that this medicine (estradiol valerate) is indeed helpful. Although she still suffers from sleep disturbances and is at times nervous and irritable, she no longer has these "terrible depressions." She hardly ever thinks of suicide and is full of hope for the future.

After Three Weeks of Treatment: After an administration of 130 mg. of estradiol valerate, the patient reports that her depressions have almost completely ceased. She can now do many types of work which heretofore were even impossible for her to start. She can sleep much better than before. Her appetite is good. She has gained at least two pounds. She is making plans for the future (she intends to go to lectures at the university). She is surprised that many things do not upset her any more. From time to time she has a feeling of happiness although there is no special cause for this.

Conclusion: The patient has shown marked improvement during the estradiol valerate treatment. There has been an improvement in her thoughts of depression, her disposition, her functional capacity, and even in her sleep disturbances. No occurrence of side effects or other findings has been observed.

EXAMPLE 6

The patient is a 41-year-old married female who has suffered from depressive phases for the last 20 years. She cannot remember when the first depressive phase occurred. Fifteen years ago she was treated for depressions as an inpatient and received a series of electroshock treatments. During the subsequent depressive phases she received various medicaments, such as chlorpromazine, amitryptiline, and imipramine preparations. The electroshock treatment was probably quite successful, but she is greatly afraid of this treatment. Relief was obtained by treating her with medicines, but her depressive disposition did not improve to any great extent. During the past months her cycles were very irregular, which bothered her greatly. Additionally, her mood was one of depression.

Prior to Treatment: The patient appears upset, nervous, restless; her facial expression is troubled and anxious. She states that she is very dejected; in particular, she feels very unhappy and troubled upon getting out of bed in the morning. She does not know at all how to solve the everyday problems. However, during the course of the day her disposition improves, she feels less dejected and nervous. Although she goes to sleep quickly, she wakes up frequently during the night and very early the next morning. She then cannot go back to sleep any more. She makes an exhausted impression. During the past years, her libido was nil, and she had no desire for any other social contacts. She does not even have the wish of telephoning her best friends or her parents. During the past years she lost many of her best friends in succession. Her husband is very busy. He frequently does not have the time to sit down and talk to her. Once they speak with each other, he soon becomes impatient and they enter into violent quarrels. He attempts to gain help from the children. As for the children's needs, those are filled by the mother, but she does not have the patience to talk with them for any length of time or to help them. She feels helpless and worthless. She has difficulties concentrating; in particular, her memory is impaired. She must write down everything that has to be done, but then she forgets where she wrote it down.

After One Week of Treatment: (40 mg. of estradiol valerate.)

The patient seems to show no improvement. She reports that she had set her hopes in the "hormone" treatment, but that she is now disappointed. During the past week she had two violent disputes with her husband. Everything seemed to have gone wrong during this week. Her mother called her, telling her she felt ill and asked her to come. However, she could not go to her mother. As a consequence, she felt bad and guilty. Her husband feels that the hormone treatment is not helpful and proposes that she be treated by electroshock as an inpatient. The patient is informed that it is still too early to make a decision on whether or not the treatment was successful. She agrees to continue the treatment for another week. She receives a prescription for three times 2 mg. of estradiol valerate per day for the following week.

After Two Weeks of Treatment: (82 mg. of estradiol valerate.)

In today's session, the patient indicates a certain contentedness. She appears more rested and not as jumpy and upset as previously. She reports that the past week was rather strenuous for her. Yet, in spite of her exertions, she surprisingly does not feel too exhausted. Although in general she still does not convey a happy impression, she seems less discouraged and somewhat more hopeful. Her sleep also improved slightly. She now can sleep for 6–7 hours. She feels rather well in the morning. When she woke up three days ago she surprised herself by being able to make plans for the day. She was quite enthusiastic and full of energy. Even her husband told her that the "hormone treatment" was of help, after all, and that she should continue the treatment.

After Three Weeks of Treatment: (122 mg. of estradiol valerate.)

The patient reports that she has only very minor depressions during the day as well as in the morning. She confirms that she had placed only little hope in a hormone treatment. However, after the second week and especially after the last week she has revised her opinion. In spite of her fear that the hormone could cause cancer, she wishes to continue the treatment. Her depressive mood has clearly improved, the improvement being spontaneous in a certain way. However, she feels that the improvement is due to the hormone treatment. Since she has suffered from depressive conditions for such a long period of time, she is incapable of deciding whether the improvement is due to the treatment or occurred spontaneously. The astonishing aspect is that she has no troublesome side effects, such as fatigue, dizziness, or blurred vision.

Conclusion: Estradiol valerate definitely exerted an antidepressant effect on this patient. The onset of efficacy began relatively gradually and not too markedly. After the second week of treatment, and particularly after the third week of treatment, the patient showed a clear improvement in depressive symptoms. No side effects were observed. The treatment is being continued.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of treating depression in a human suffering from depression which is not caused by an estrogen deficiency, comprising administering to the human an anti-depressantly effective amount of estradiol valerate.

2. The method of claim 1, wherein the depression from which the human is suffering is also not caused by any other endocrinological disturbance.

3. The method of claim 1, wherein the human is a female.

4. The method of claim 1, wherein the daily dosage is 1-100 mg.

5. The method of claim 4, wherein the daily dosage is 2-8 mg.

6. The method of claim 1, wherein the depression is an endogenic, neurotic or reactive depression, a depression due to age or an involution depression.

7. A method of treating psychic disturbances in a human, said human displaying at least one of the following symptoms: weakness of concentration ability and memory; diminishing of general functional capacity; fatigue; loss of interest; sleep disturbances; insomnia at night with fatigue during the day; or loss of libido and potency in young patients without steroid hormone deficiency; and not suffering from depression which is caused by an estrogen deficiency, said method comprising administering to the human an amount of estradiol valerate effective to ameliorate the psychic disturbance.

8. A method of claim 1 wherein the human so treated is not otherwise in need of treatment with estradiol valerate.

9. A method of claim 3 wherein the female human so treated is not suffering from the climacterium.

* * * * *